United States Patent [19]

Pugia

[11] Patent Number: 5,399,498
[45] Date of Patent: Mar. 21, 1995

[54] REDUCTION OF BACKGROUND INTERFERENCES IN THE MOLYBDATE-DYE PROTEIN ASSAY

[75] Inventor: Michael J. Pugia, Granger, Ind.

[73] Assignee: Miles Inc., Elkhart, Ind.

[21] Appl. No.: 168,220

[22] Filed: Dec. 17, 1993

[51] Int. Cl.$^6$ ............................................. G01N 33/00
[52] U.S. Cl. .................................... 436/86; 422/56; 436/15; 436/63; 436/87; 436/88; 436/169
[58] Field of Search ..................... 422/56, 57; 436/63, 436/15, 66, 67, 86, 88, 87, 166, 169, 175, 103, 104, 105

[56] References Cited

U.S. PATENT DOCUMENTS

| | | | |
|---|---|---|---|
| 4,960,710 | 10/1990 | Lau ........................................ | 436/86 |
| 5,055,407 | 10/1991 | Lau et al. ............................. | 436/2 |
| 5,087,575 | 2/1992 | Lau ........................................ | 436/166 |
| 5,173,431 | 12/1992 | Pugia et al. ......................... | 436/86 |

*Primary Examiner*—Donald E. Czaja
*Assistant Examiner*—Lien Tran
*Attorney, Agent, or Firm*—Jerome L. Jeffers

[57] ABSTRACT

Disclosed is an improvement to the assay for protein in urine involving the use of a molybdate or tungstate salt and an indicator dye which forms a complex with molybdate or tungstate whose absorption band is shifted in the presence of protein. The improvement involves the use of an ionizable phosphate containing compound characterized by the formula:

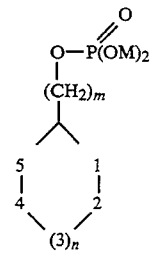

to reduce background interference caused by constituents normally present in urine.

10 Claims, No Drawings

REDUCTION OF BACKGROUND INTERFERENCES IN THE MOLYBDATE-DYE PROTEIN ASSAY

BACKGROUND OF THE INVENTION

Various methods for the determination of protein in aqueous fluid have been reported in the literature. These methods include the Kjeldahl method, biuret method, Lowry method, dyestuff combination method, UV method and fluorometric method. Widely used methods for the assay of urinary protein are the Kingbury-Clark method; reported in J. Lab. Clin. Med., 11, 981 (1926); the Exton method; reported in Rinsho Byori, 15, 699 (1967); Merlemans method; reported in Clin. Chim. Acta, 5, 757 (1960) and the Coomassie brilliant blue method; reported in Anal. Biochem., 72, 248 (1976).

In general, protein interacts with various substances, particularly with dyes such as bromphenol blue, coomassie brilliant blue and eosine as well as metal ions such as silver (I), copper (II), zinc (II) and lead (II). Typically, the addition of protein to the reaction between a dye and a metal ion gives a spectral change to a dye-metal ion solution. Fujita et al report in Bunseki Kagaku Vol. 32, Pp. E379-E386 that the addition of protein to the reaction between pyrogallol red and molybdenum (VI) produces a different spectrum than that of the pyrogallol red-molybdenum (VI) complex solution. These authors report that among metal ions tested, large amounts of iron (II) interfered with the protein determination and that among anions tested, organic acids such as citrate, oxalate and tartrate ions decreased the absorbance at 600 nm. While large amounts of other ions did not interfere, Fujita et al report that large amounts of creatinine and amino acids caused a slight increase in absorbance at 600 nm.

Japanese Kokai Patent No. SHO 62[1987]-6170 discloses a test strip for protein determination comprising a molybdate salt, a pigment which forms a complex with molybdate and whose adsorption band is shifted in the presence of a protein and a chelating agent which combines with molybdate ions. A similar assay for trace amounts of protein is disclosed in Japanese Kokai Patent 61-155757 in which there is described the use of a chelating agent which is able to bond with molybdenum or a metal ion which is able to bond with oxalic acid, citric acid, phosphoric acid or their salts which are normally present in the test sample. This assay is a dye binding method using the complex of pyrogallol red and molybdenum. At low pH the dye-metal complex is red. The color changes to blue when deprotenated at higher pH. The protein causes the dye to deprotonate more easily (at a lower pH) by the interaction of positively charged amino acid groups stabilizing the negatively charged deprotonated dye-molybdate complex.

The major limitation to the transition metal-pyrogallol red method of protein detection is the interference of chelating agents and nitrogen compounds normally found in urine. Background color or the color without protein is also dependent on urinary interfering compounds. Citrate, phosphate, tartrate and oxalate shift the dye-metal complex to a red color (protonated form in Scheme I).

SCHEME I

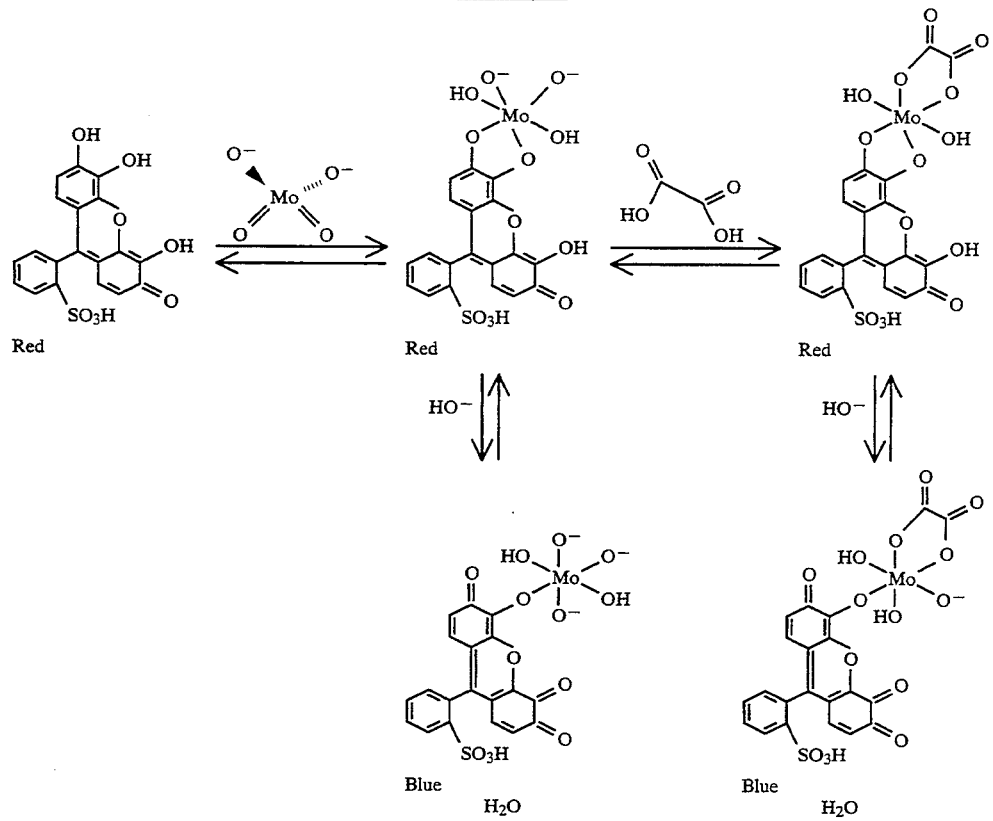

The extent of the shifts is given in Tables 1–3; the direction of the shift is given below in Table A. Presumably the carboxylic acid groups complex the metal to stabilize the red protenated form.

TABLE A

| Ion | Affect on Blue Color of Background |
|---|---|
| Ammonium | No effect |
| Oxalate | Decreases relative to water |
| Creatinine | No effect |
| Citrate | Decreases relative to water |
| Phosphate | Decreases relative to water |

Creatinine and amino acids such as glycine shift the complex to blue (deprotonated form). This effect is the same as that observed with protein. To observe this effect, the creatinine concentration must be higher than the range tested in Tables 1-3 which represents the physiological extremes in urine. These interferences have been reduced by the use of chelating agents or metal ions which do not react with the dye. Two Japanese patents to Wako Ltd. describe the use of certain chelates and metals to reduce interferences. These patents, 62[1987]-6170 and 61-155757 (1986) cite oxalic acid as the preferred species for limiting interferences associated with the use of molybdate-pyrogallol red reagents.

It has more recently been discovered that tungstate acts in a manner similar to molybdate in the presence of protein and a dye. Useful tungstate salts include sodium tungstate, potassium tungstate, lithium tungstate, ammonium tungstate or a tungstate with an alkyl, dialkyl, trialkyl or tetraalkylammonium ion or a phosphotungstate bearing a similar cation.

SUMMARY OF THE INVENTION

The present invention is an improvement to the assay for the determination of a protein in urine involving the use of a molybdate or tungstate salt and a dye which forms a complex with molybdate or tungstate, the absorption band of which is shifted in the presence of protein. The improvement comprises the introduction to the reaction medium of an ionizable phosphate containing compound of the formula:

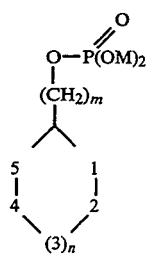

wherein 2, 3, 4 and 5 are selected from the group consisting of

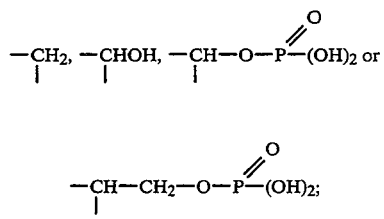

1 is any of the above or —O— and m and n are independently 0 or 1, in sufficient quantity to reduce background interference while allowing the protein/molybdate/dye indicator response to proceed.

DESCRIPTION OF THE INVENTION

The use of phytic acid, and/or certain derivatives thereof as circumscribed by the foregoing formula (I), for the reduction of background interference can be applied to the pyrogallol red molybdate method for determining urinary proteins. The pyrogallol red method is a total protein chemistry, i.e. the response is not dependent on the type of protein. For example, human serum albumin (HSA) at 15 mg/dL provides the same response as IgG at 15 mg/dL. The reaction sequence by which the molybdate (VI) ion, pyrogallol red and protein interact to provide a detectable response for protein in an aqueous fluid, such as urine, is as set out in Scheme I.

There exists, however, the previously discussed problem with background interference caused by foreign substances normally found in urine. It has been discovered that the introduction of phytic acid into the system can reduce these background interferences enough to permit the detection of urinary protein at a level as low as 5.0 mg/dL. While there is no intent to be bound by any particular theory or mechanism of how the present invention accomplishes the desired result of reducing background interference, it is believed that the phytic acid or derivative thereof reduces interference by reducing wavelength shifts caused by oxalate, citrate, creatinine and amino acids typically present in urine. The phytic acid is believed to reduce these wavelength shifts by causing a shift in the color to red by one of its negatively charged groups stabilizing the dye-metal form by complexation with molybdate as indicated by Scheme II. All of the compounds circumscribed by Formula I contain at least one negative charge for complexation which are attached to the ring. Representative compounds of this group are similar to phytic acid in that they all demonstrate some degree of precipitation of (or interaction with) the dye-molybdate-protein complex and some extent of a wavelength shift to red.

SCHEME II

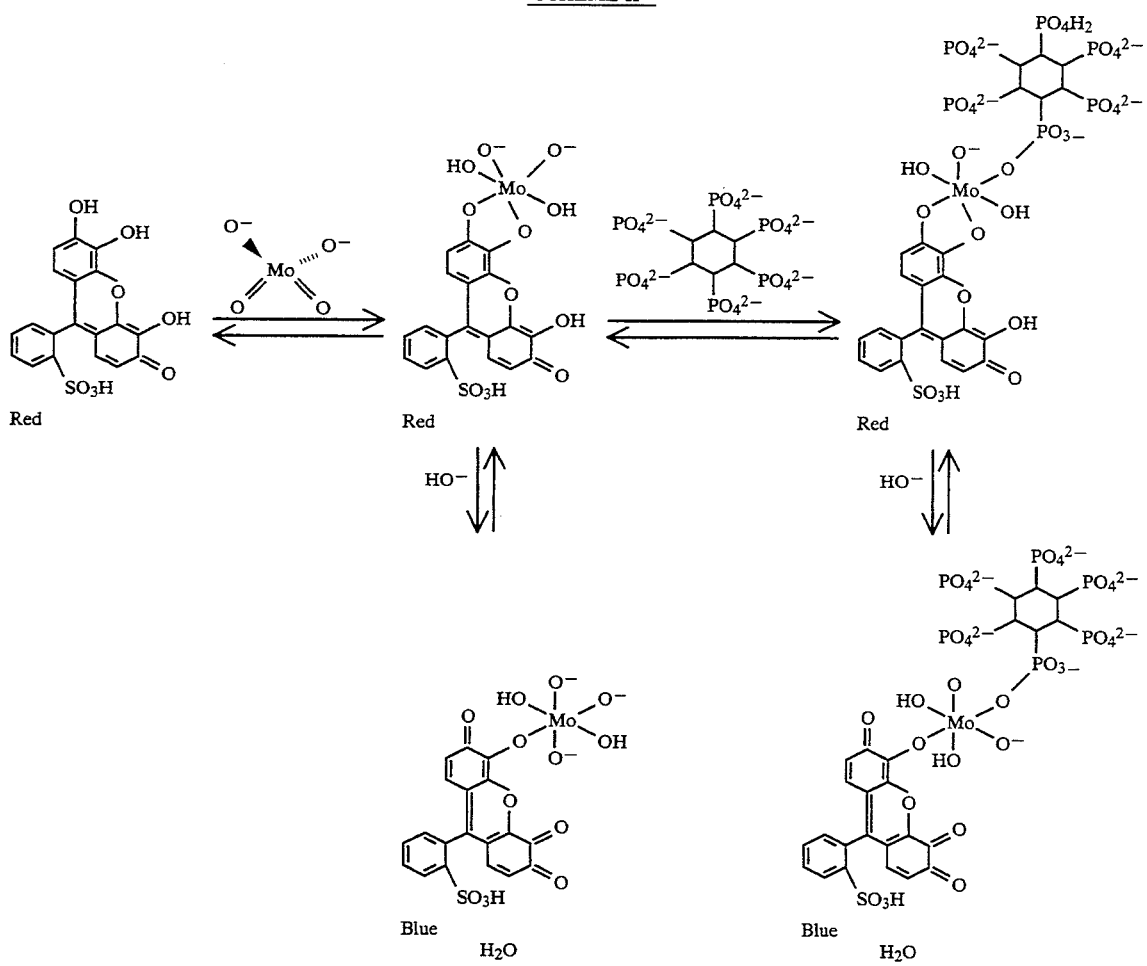

Phytic acid enhances the protein response (compare Table 2 to Table 1). The binding of molybdate and/or tungstate by phytic acid increases the negative charge carried by the molybdate and increases association between the positively charged amino acid groups and the negatively charged deprotonated dye-molybdate complex. In doing so, the binding becomes stronger and less dependent upon the ability of the protein to include the metal-dye (inclusion, intercalation, absorption) and the assay becomes more of a total protein assay. Simple phosphates, in the absence of phytic acid or its derivatives as set out in Formula (I), behave in a manner similar to oxalate in that they inhibit the protein response and cause unequal responses between HSA and IgG. The pyrophosphates listed in Japanese Kokai Patent No. 61-155757 are multiple charged phosphates, however, they do not enhance and equalize the protein responses. This may be due to their hydrolysis to simple phosphates upon contact with water. This may also be due to the lack of a ring structure in simple phosphates since the ring of phytic acid influences the ability of the protein to include the metal-dye complex.

This mechanism of action is not limited to systems which use pyrogallol red. Any dye which forms a complex with molybdate whose absorption band is shifted in the presence of protein may be employed. Accordingly, suitable dyes include those dyes which include both protein and metal binding properties and in which a shift of the absorption maxima is induced in the presence of protein. Suitable dyes include pyrocatechol violet (preferred for use with tungstate salts); brompyrogallol red; o-hydroxyhydroquinonephthalein; tetrachlorogallein; vylidyl blue; 6,7-dihydroxy-2,4-diphenylbenzopyrillium chloride; chrome azurol 5; alizarine yellow R (C.I. mordant orange 1); eriochrome black T (C.I. mordant black 11); Neolan blue 2G (C.I. acid blue 158); Irgalan grey BL (C.I. acid black 58); 1-2',4'-dihydroxyphenylazo-5-chloro-2-hydroxybenzene-3-sulfonic acid; coprantine violet BLL (C.I. direct violet 82); benzo fast copper red GGL (C.I. direct red 180); pigment green B (C.I. pigment green 8) and napthol green (C.I. acid green 1).

The present invention can be performed as a solution assay by mixing equal amounts of reagent and sample, measuring the resulting absorbance at 580 nm and converting the absorbance to protein concentration against a standard curve. Typically, the present system is used as a test strip in the form of an absorbent bibulous or non-bibulous support to which the reagents are applied by dipping the strip substrate in their solution with subsequent evaporation of the carrier liquid. Typically an aqueous solution is used although polar organic solvents such as methanol, ethanol and acetonitrile may be used as solvent for the reagents. The absorbent carrier substrate used for the test strip is composed of materials commonly used as carriers such as paper, cellulose, fabrics made of synthetic resin, i.e. nylon, or unwoven fabric. The absorbent material is typically bound to a layer of support material such as glass fiber, or a synthetic polymer sheet to provide structural support.

The method of practicing the present invention is further illustrated by the following examples:

EXAMPLE I

A solution of pyrogallol red, molybdate and succinic acid was prepared as follows:

|  | Conc. Used mM | Allowable mM Range |
| --- | --- | --- |
| 25 mL Methanol | — | — |
| 475 mL Water | — | — |
| 700 mg Pyrogallol Red | 3.4 | 0.03–10.0 |
| 3000 mg Molybdate (VI) | 4.85 | 0.05–10.0 |
| 5.9 g Succinic Acid* | 100 | 0.0–1000 |
| pH (for all solutions) | 1.5 | 1.0–3.0 |

*Succinic acid was used in all the formulations reported herein as a non reactive buffer. Its presence is not required when phytic acid is present since phytic acid can function as a buffer as well.

Background interferences for various interferants commonly found in urine were determined by the addition of known interferants at the physiological extremes expected in urine. The changes in color from water lacking interferant was measured. Protein responses for both HSA and IgG were determined by the addition of 50 mg/dL protein to a solution of urine containing or lacking interferant. The change in color from the same solution lacking protein was measured using a Research Products Rapid Reflectance Scanner. The results of this experiment are summarized in Table 1. In a separate experiment, a formulation prepared as above, except that phytic acid was added at a level of 2.5 g/L (15 mM), was tested. The results of this experiment are summarized in Table 2.

TABLE 1

|  |  | Background | Delta $E^1$ Protein Response HSA | IgG |
| --- | --- | --- | --- | --- |
| Water |  | 0.0 | 8.8 | 6.8 |
| Interferant in water |  |  |  |  |
| Ammonium chloride | 200 mg/dL | 2.1 | 7.6 | 6.7 |
| Oxalate | 75 mg/dL | 10.8 | 7.9 | 8.2 |
| Creatinine | 400 mg/dL | 3.8 | 9.1 | 8.7 |
| Citrate | 224 mg/dL | 9.5 | 8.1 | 6.0 |
| Phosphate | 3830 mg/dL | 10.9 | 6.1 | 7.3 |
| High SG Urine[2] |  | 12.2 | 5.1 | 4.3 |
| Low SG Urine |  | 8.1 | 6.3 | 4.1 |

TABLE 2

|  |  | Background | Delta $E^1$ Protein Response HSA | IgG |
| --- | --- | --- | --- | --- |
| Water |  | 0.0 | 10.7 | 8.6 |
| Interferant in water |  |  |  |  |
| Ammonium chloride | 200 mg/dL | 1.4 | 11.2 | 10.2 |
| Oxalate | 75 mg/dL | 2.7 | 13.2 | 11.8 |
| Creatinine | 400 mg/dL | 2.3 | 11.6 | 13.3 |
| Citrate | 224 mg/dL | 3.3 | 12.9 | 10.6 |
| Phosphate | 3830 mg/dL | 2.9 | 15.9 | 14.2 |
| High SG Urine[2] |  | 2.3 | 13.9 | 12.9 |

TABLE 2-continued

|  | Background | Delta $E^1$ Protein Response HSA | IgG |
| --- | --- | --- | --- |
| Low SG Urine | 3.1 | 14.5 | 13.5 |

[1]Delta E represents the change in color as calculated from L*, a*, b* values between two levels using the following: Delta E = $((L^*_1 - L^*_2)^2 + (a^*_1 - a^*_2)^2 + (b^*_1 - b^*_2)^2)^{0.5}$
The Delta E from the background is calculated as the change from water. The Delta E for protein response is calculated as the change from same solution or urine lacking protein. The protein concentration for this study was 5.0 mg/dL.
[2]The high SG urine had a specific gravity of 1.022 while the low SG urine had a specific gravity of 1.007. Both urines were adjusted to a pH of 1.5 to negate any difference in buffer capacity between formulas.

From the data presented in Tables 1 and 2, it can be determined that the color of the dye-metal complex with protein (protein response) is also dependent on citrate, phosphate, tartarate, oxalate, creatinine and amino acids. Compounds which influence the background will have the same effect in the presence of protein. The extent of the shifts corrected for background is set out in Tables 1–3. There was no effect of the urinary interfering compounds after the protein response was corrected for background and when the concentration of these compounds was no higher than the physiological extremes in urine. Additional effects were observed even after correcting for background when concentrations were higher than the range tested in Table 1 which are the physiological extremes in urine.

EXAMPLE II

In a separate experiment, a test solution of oxalic acid, pyrogallol red, molybdate and succinic acid was prepared as described in Example I except that oxalic acid was added at a level of 1 gm/L. This solution was tested for background interference and HSA/IgG protein response as in Example I. The results of these tests are set out in Table 3.

TABLE 3

|  |  | Background | Delta $E^1$ Protein Response HSA | IgG |
| --- | --- | --- | --- | --- |
| Water |  | 0.0 | 8.4 | 5.5 |
| Interferant in water |  |  |  |  |
| Ammonium chloride | 200 mg/dL | 2.5 | 8.2 | 4.7 |
| Oxalate | 75 mg/dL | 2.1 | 8.4 | 6.4 |
| Creatinine | 400 mg/dL | 1.4 | 6.7 | 4.6 |
| Citrate | 224 mg/dL | 2.3 | 9.1 | 5.0 |
| Phosphate | 3830 mg/dL | 3.1 | 8.6 | 5.5 |
| High SG Urine |  | 4.6 | 7.7 | 4.2 |
| Low SG Urine |  | 2.1 | 8.4 | 4.9 |

These studies show that both oxalic and phytic acid can reduce background interference, i.e. wavelength shifts caused by oxalate, citrate, creatinine and ammonium. The use of oxalate to reduce oxalate interference is a common practice called masking. If the interfering compound is already present in excess and more is added via the test sample, little, if any, additional change is observed. The assay with excess oxalate is made operational by adjusting the pH to compensate for the shift to red metal-dye caused by oxalate. However, the use of phytic acid increases the protein response whereas the use of oxalic acid does not. Additionally, the response between proteins is nearly equal with phytic acid but unequal in the presence of oxalic acid since oxalate reduces the response of IgG whereas phytic acid does not. It was also found that phytic acid precipitated the dye-molybdate complex upon the addition of protein. This effect can be used to separate or to isolate the protein or to concentrate the color on the read surface. This effect may also be responsible for stabilizing the protein bound dye-metal-phytic acid complex. When excess oxalate (as in Table 3) is present, the oxalate reduces the protein response. The binding of molybdate by oxalate reduces the negative charge carried by the molybdate. This reduces associations between the positively charged amino acid groups and the negatively charged deprotonated dye-molybdate complex. In doing so the binding becomes more dependent on the ability of the protein to include the dye into its structure and the assay becomes less sensitive. The assay also becomes more specific for human serum albumin which is more readily able to form inclusion complexes with triphenylaryl dyes.

What is claimed is:

1. In an assay for the determination of a protein in urine which uses a molybdate or tungstate salt and a dye which forms a complex with molybdate or tungstate ion wherein the absorption band of the complex is shifted in the presence of protein to provide a detectable response, the improvement which comprises introducing an ionizable phosphate containing compound of the formula:

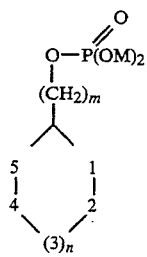

wherein 2, 3, 4 and 5 are selected from the group consisting of

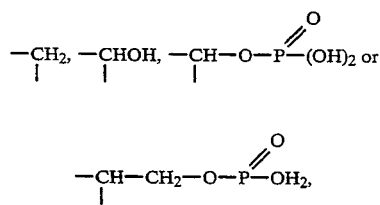

M is H, 1 is any of the above or —O— and m and n are independently O or 1, in sufficient quantity to reduce background interference while allowing the protein/molybdate/dye or protein/tungstate/dye detectable response to proceed.

2. The assay of claim 1 wherein the ionizable phosphate containing compound is phytic acid.

3. The assay of claim 1 wherein the salt is a molybdate.

4. The assay of claims 1, 2 or 3 wherein the dye is pyrogallol red.

5. The assay of claim 4 wherein the protein is human serum albumin.

6. The assay of claim 1 wherein the dye is pyrocatechol violet; brompyrogallol red; o-hydroxyhydroquinonephthalein; tetrachlorogallein; vylidyl blue; 6,7-dihydroxy-2,4-diphenylbenzopyrillium chloride; chrome azurol 5; alizarine yellow RC; eriochrome black T; Neolan blue 2G; Irgalan grey BL; 1-2',4'-dihydroxyphenylazo-5-chloro-2-hydroxybenzene-3-sulfonic acid; coprantine violet BLL; benzo fast copper red GGL or napthol green.

7. The assay of claim 1 wherein the molybdate or tungstate salt, dye and ionizable phosphate containing compound are contacted with the urine in the form of their solution in a suitable solvent.

8. The assay of claim 1 wherein the molybdate or tungstate salt, dye and ionizable phosphate containing compound are dried onto an absorbent support material before being contacted with the urine.

9. A composition of matter suitable for the determination of protein in urine which comprises:
 a) a molybdate or tungstate salt;
 b) a dye which forms a complex with molybdate or tungstate ion whose absorption band is shifted in the presence of protein; and
 c) an ionizable phosphate containing compound of the formula:

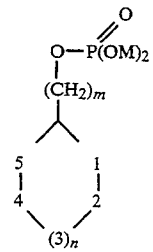

wherein 2, 3, 4 and 5 are selected from the group consisting of

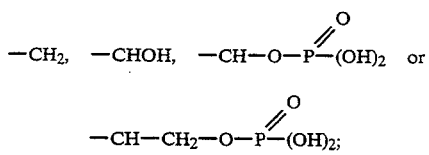

M is H, 1 is any of the above or —O— and m and n are independently O or 1.

10. The composition of claim 9 wherein the salt is a molybdate and the phosphate containing compound is phytic acid.

* * * * *